United States Patent [19]

Ivey, Jr. et al.

[11] Patent Number: 5,969,615

[45] Date of Patent: Oct. 19, 1999

[54] SYSTEM FOR MONITORING AND ENCUMBERING USE OF A HAND-OPERATED MACHINE BY AN IMPAIRED INDIVIDUAL THROUGH DETECTION OF TOXINS IN THE INDIVIDUAL

[76] Inventors: Ellwood G. Ivey, Jr., The DUIE Project, 1730 E. 33rd St., Savannah, Ga. 31404; Michael L. Horovitz, 1410 Forsyth Rd., Savannah, Ga. 31406; Cedric Stratton, 3605 Oakland Dr., Savannah, Ga. 31404

[21] Appl. No.: 09/067,720

[22] Filed: Apr. 28, 1998

Related U.S. Application Data

[63] Continuation-in-part of application No. 08/050,947, Apr. 22, 1993, Pat. No. 5,793,292.

[51] Int. Cl.[6] .................................................. G08B 21/00
[52] U.S. Cl. ......................... 340/576; 180/272; 600/346
[58] Field of Search .......................... 340/576; 180/272; 600/346

[56] References Cited

U.S. PATENT DOCUMENTS

| | | | |
|---|---|---|---|
| 3,886,540 | 5/1975 | Sussman et al. ....................... | 180/272 |
| 4,093,945 | 6/1978 | Collier et al. ......................... | 180/272 |
| 4,613,845 | 9/1986 | Du Bois ................................. | 340/576 |
| 4,617,559 | 10/1986 | Slansky ................................. | 340/576 |
| 4,846,182 | 7/1989 | Fogt et al. ............................. | 600/362 |
| 4,957,108 | 9/1990 | Schoendorfer et al. ................ | 600/362 |
| 4,960,467 | 10/1990 | Peck ..................................... | 252/408.1 |
| 4,997,770 | 3/1991 | Giles et al. ............................ | 436/132 |
| 5,050,604 | 9/1991 | Reshef et al. ......................... | 600/346 |
| 5,113,860 | 5/1992 | McQuinn .............................. | 600/345 |
| 5,220,919 | 6/1993 | Phillips et al. ........................ | 600/345 |
| 5,531,225 | 7/1996 | Nawata et al. ........................ | 340/576 |
| 5,793,292 | 8/1998 | Ivey, Jr. ................................ | 340/576 |

*Primary Examiner*—Glen Swann
*Attorney, Agent, or Firm*—Michael Drew

[57] ABSTRACT

A portion a the machine which the operator regularly engages with his or her hands has incorporated therein a plurality of passageways (14) through which a vacuum is applied to draw vapor which is emitted by the hands of the individual. Vapor from the individual's hands is drawn through a sampling apparatus. The sampling apparatus contains an electrical coil (32, 36, 42, 46) which is coated with a composite metal-nonmetal catalytic substance which causes ethanol to oxidize at the coil. When ethanol-containing vapor passes over the coil, oxidation at the coil causes an electrical charge to build up on the coil. The charge build-up is detected and processed in a discriminating type of electrical circuit which incorporates a wheatstone bridge or a constant-current loop. The resulting signal is further processed then ultimately used to estimate the alcohol content of the individual.

14 Claims, 3 Drawing Sheets

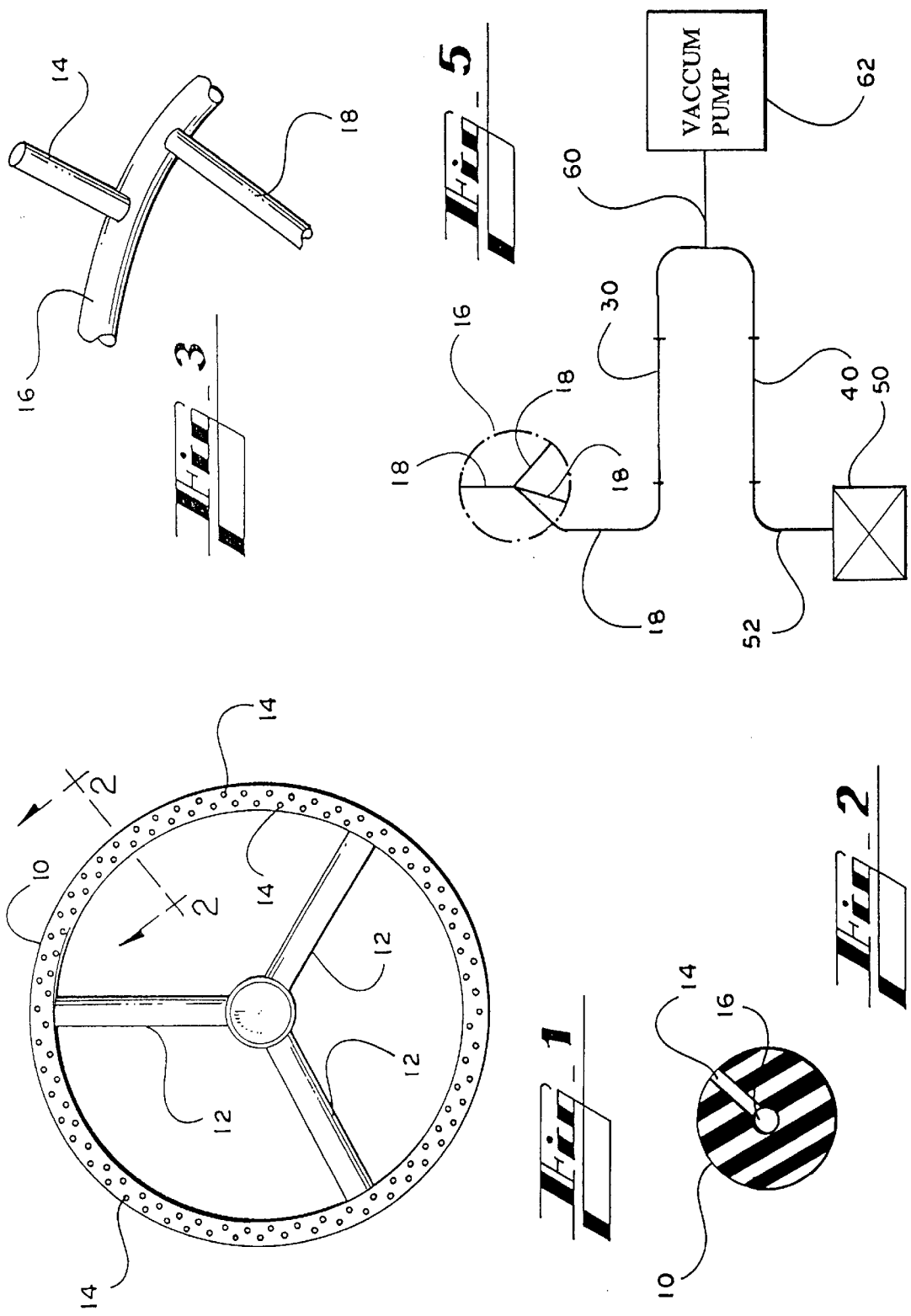

SYSTEM FOR MONITORING AND ENCUMBERING USE OF A HAND-OPERATED MACHINE BY AN IMPAIRED INDIVIDUAL THROUGH DETECTION OF TOXINS IN THE INDIVIDUAL

RELATED APPLICATIONS

This application is a continuation-in-part of U.S. patent application Ser. No. 08/050,947 filed Apr. 22, 1993, issued as U.S. Pat. No. 5,793,292.

TECHNICAL FIELD OF THE INVENTION

The present invention relates to a system integrated into a hand-operated machine, such as a motor vehicle, that non-invasively detects in an operator of the machine the presence of toxins associated with performance impairing substances such as alcohol, and facilitates subsequent encumbrance of the operation of the machine upon the detection of a toxin.

BACKGROUND OF THE INVENTION

The presence and levels of certain types of toxins in the body of an individual is indicative of the consumption of certain substances which are known to impair the performance capability of an individual. In industry, the level of certain toxins in the body of an employee is used to determine the employee's capability to perform on the job, whether the employee can perform the job safely and whether the employee is in compliance with company policy regarding use Of substances (such as alcohol or cocaine) which produce the toxins. In the medical field the presence of toxins is known to aid in the determination of the origin of loss of motor function and life-threatening coma. In the legal field the specific level of certain toxins in the blood stream is used as an objective indicia of fitness to operate machinery or to drive an automobile or other vehicles. It is particularly important for law enforcement purposes to have simple, fast, convenient, automated qualitative methods of determining whether there are toxins in an individual's blood system such as alcohol and cocaine or metabolites of such substances.

Known methods of integrating a toxin-testing device into a vehicle have been problematic. Examples of such problematic devices are disclosed in U.S. Pat. No. 4,093,945 and U.S. Pat. No. 3,886,540.

SUMMARY OF THE INVENTION

The present invention provides a passive, non-invasive means for detecting the presence of toxins related to performance-impairing substances in an operator of a hand-operated machine.

In a system for monitoring and encumbering use of a hand-operated machine by an impaired individual through detection of toxins in the individual according to a preferred embodiment of the invention a portion of the machine which the operator regularly engages with his or her hands has incorporated therein a plurality of passageways through which a vacuum is applied to draw fluidized perspiration, generally in the form of vapor, which is emitted by the hands of the individual. Vapor from the individual's hands is drawn through a sampling apparatus. The sampling apparatus contains an electrical coil which is coated with a metal-nonmetal catalytic substance which causes ethanol to oxidize at the coil. When ethanol-containing vapor passes over the coil, oxidation at the coil causes a negative electrical charge to build up on the coil. The charge build-up is detected and processed in a discriminating type of electrical circuit which incorporates a wheatstone bridge or a constant-current loop. The resulting signal is further processed then ultimately used to estimate the alcohol content of the individual. If the alcohol content exceeds a predetermined level which is indicative of intoxication circuitry is energized which causes actuation of mechanisms which encumber operation of the machine.

Other aspects, objects, features, and advantages of the present invention will become apparent to those skilled in the art upon reading the detailed description of preferred embodiments.

BRIEF DESCRIPTION OF THE DRAWINGS

FIG. 1 is an illustration of a steering wheel of a motor vehicle in a system for monitoring and encumbering use of a hand-operated machine by an impaired individual through detection of toxins in the individual according to a preferred embodiment of the invention.

FIG. 2 is a cross-section of the steering wheel of FIG. 1 taken along line 2—2 of FIG. 1.

FIG. 3 is an illustration of the vacuum tube network of the system of FIG. 1.

FIG. 5 is an illustration of the detection tube portion of a system for monitoring and encumbering use of a hand-operated machine by an impaired individual through detection of toxins in the individual according to a preferred embodiment of the invention.

DETAILED DESCRIPTION OF PREFERRED EMBODIMENTS OF THE INVENTION

Figure 6:
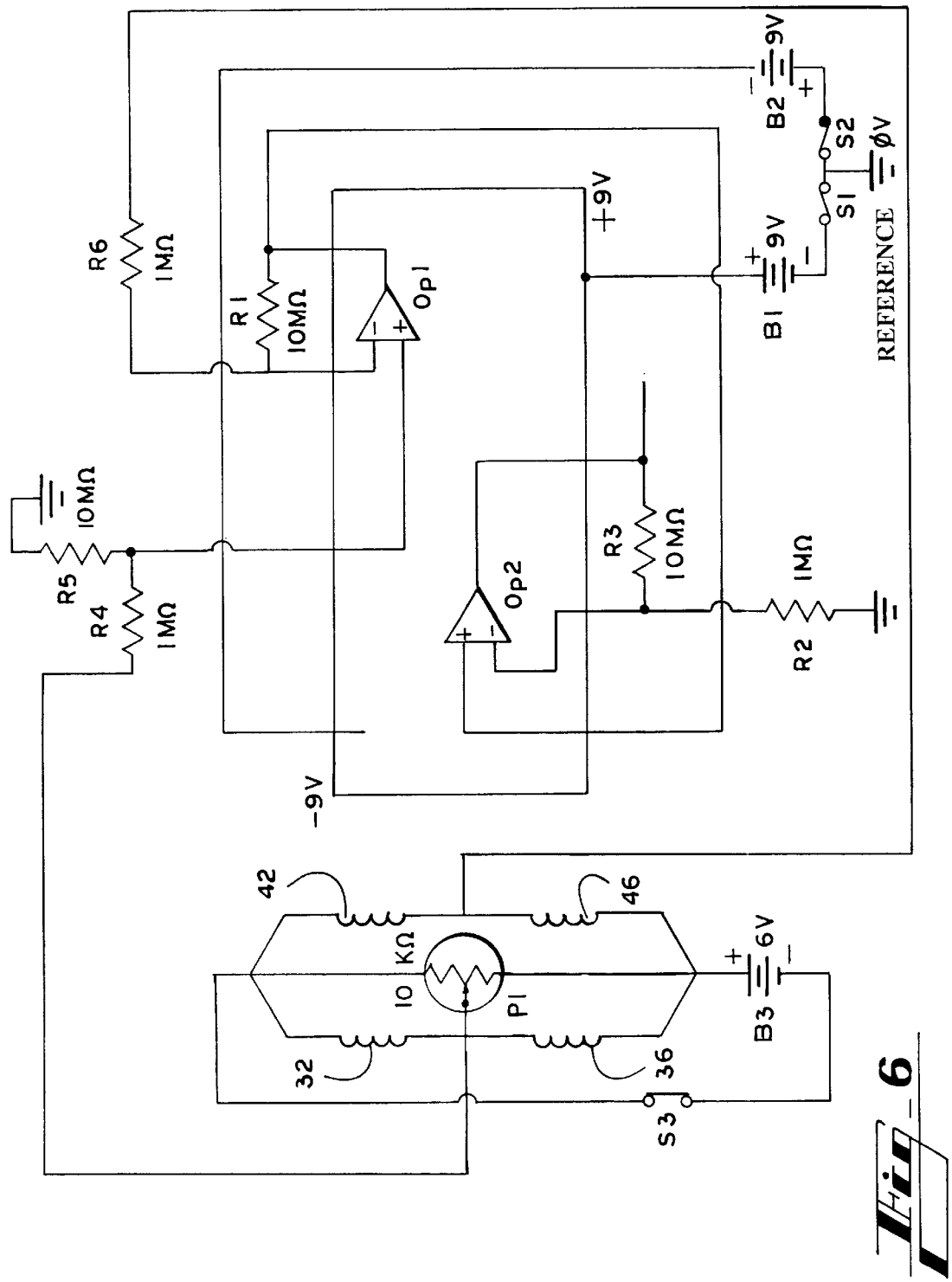
FIG. 6 is an electrical schematic diagram of the electrical components of a system for monitoring and encumbering use of a hand-operated machine by an impaired individual through detection of toxins in the individual according to a preferred embodiment of the invention.

While the specification concludes with claims particularly pointing out and distinctly claiming the subject matter which is regarded as the present invention, the invention will now be described with reference to the following description of embodiments taken in conjunction with the accompanying drawings.

The present invention provides a system for utilizing the biological characteristics of humans together with the pharmacological characteristics of certain performance-impairing substances to detect the presence of those performance-impairing substances in an individual, and, ultimately, to encumber the individual's ability to continue operation a machine when such a substance is detected. Encumbrance of the operation of the machine in general includes any means which interferes with (even though only moderately) the unfettered operation of the machine. The invention encumbers the operation of the machine by initiating a visual, audio or audio-visual mechanism which signals the operator and/or those in the vicinity of the machine that the machine may be in danger of being operated improperly. Examples of audio mechanisms are as simple as a recorded message that plays within and/or outside a motor vehicle and known circuitry which causes the horn to blow intermittently. Examples of visual signals include a warning lamp and known circuitry which causes the headlights to light intermittently. The invention is suitable for actuating mechanisms which not only signal that there may be a problem with the operation of the machine but which ultimately inhibit use of the machine, if desired. Also, as will be discussed in greater detail below, the invention signals the operator and/or others whenever proper readings cannot be taken and automatically requests that the operator take measures necessary to assure a proper reading (that is, grasp the hand-operating mechanism properly).

Most substances that are consumed by humans appear later at some point in the body (such as in bodily fluids) either in their original state or as metabolites of the original substances. The terms "consumption" and "consume" include ingesting, inhaling, injecting and transdermal absorption. Many toxins are substances which appear in the body either as a direct result of consumption of the toxin or as metabolic by-products of performance-impairing substances. For example, ethanol, which is considered a toxin, is a component of alcoholic beverages. Ethanol appears in body fluids after an alcoholic beverage has been consumed.

One of the biological characteristics utilized by the subject invention is that humans perspire. Perspiration in turn is vaporized into the air. Another important human characteristic is that many substances consumed by humans cause certain chemicals which are metabolized from the consumed substances to be secreted through the skin. Many secreted substances are vaporized in perspiration. As previously mentioned in part, alcohol is a substance which when consumed causes ethanol to be secreted in perspiration. Thus, the present invention utilizes the fact that toxins, such as alcohol, which are consumed by humans causes identifiable chemicals, such as ethanol, to be secreted in perspiration.

In a preferred embodiment of the invention vaporized perspiration is drawn through a system of tubing past a coil which has characteristics which in turn transforms ethanol in the vapor into a detectable electrical charge.

The features of the invention will now be explained in greater detail. Referring first to FIG. 1, according to a preferred embodiment of the invention an article 10 which has to be grasped by an individual to operate a machine (such as a steering wheel 10 to operate a motor vehicle) is adapted to draw fluidized perspiration, generally in the form of vapors, from the hands of the individual as the individual grasps the article (steering wheel) 10. Apertures in the steering wheel 10 are the terminating points of tubes 14 through which perspiration vapor may be drawn. Referring now also to FIG. 2, which illustrates a cross section of the steering wheel 10, and FIG. 3, which illustrates, conduit connections, the vapor tubes 14 extend from the surface of the steering wheel 10 to what may be described as a manifold tube 16 which runs axially through the steering wheel 10. The manifold tube 16 connects with at least one other collecting conduit 18 to draw the vapor through the system. As a means of support, the collecting conduits 18 may extend through the steering wheel supports 12 to tie into a further point of the conduit network. Any of the various conduits/tubes in the network may be considered fluid or vapor passageways.

Figure 4:
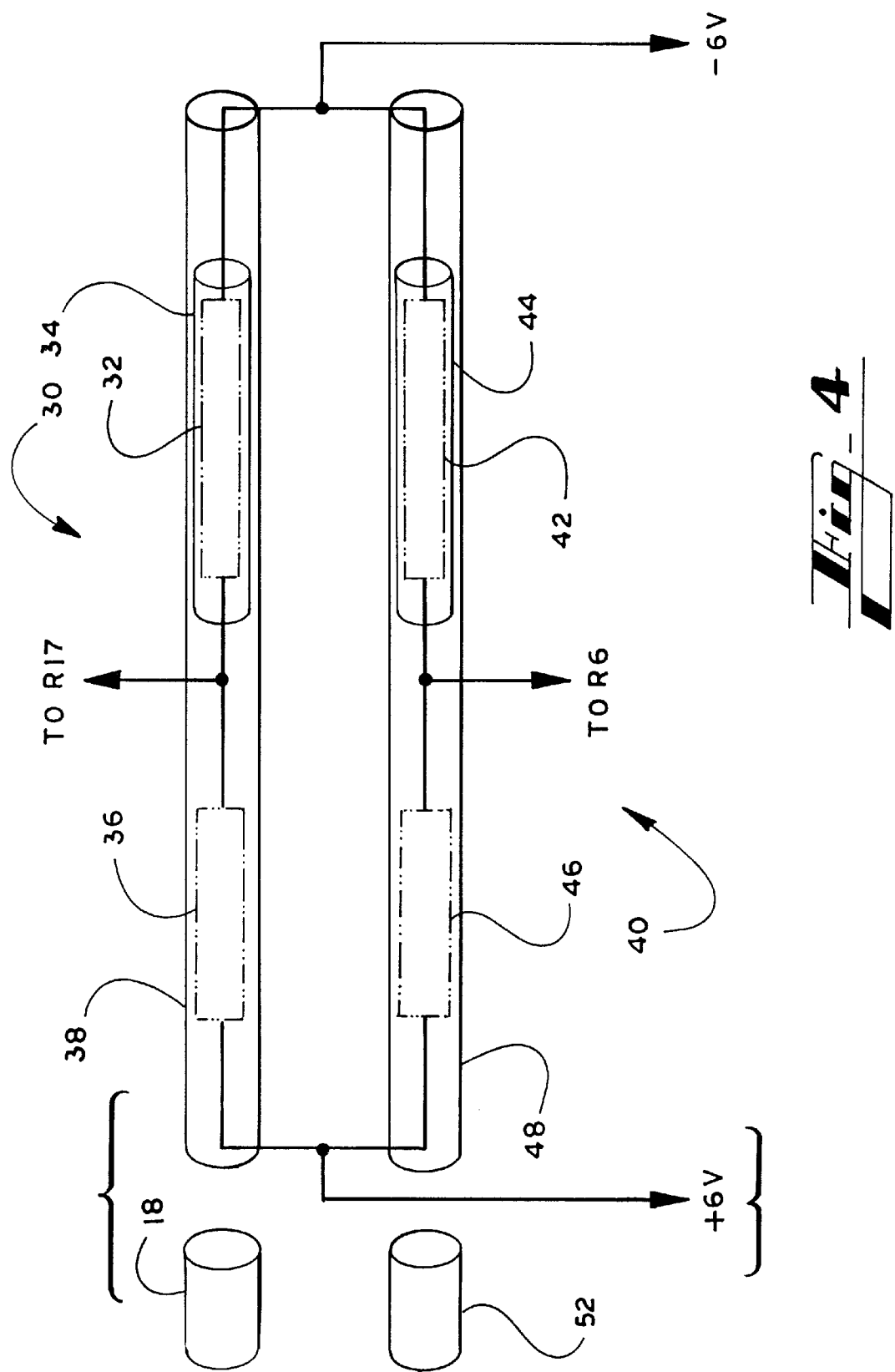
FIG. 4 is a mechanical schematic diagram of the vacuum network of the System of FIG. 1.

Referring now to FIG. 4, therein is illustrated an arrangement of sampling tubes 30, 40 to be used in conjunction with the tubing network of FIGS. 1, 2 and 3 in accordance with a preferred embodiment of the invention. In each sampling tube 30, 40 a reference coil 32, 42 is encased in tubing (such as glass capillary tubing) such that it is isolated from vapor drawn through the respective sampling tube 30, 40. A sampling coil 36, 46 is connected in series with each reference coil 32, 42. The casing 38, 48 for each sampling tube may be a respective glass tube open at each end. For convenience of reference the sampling tube which carries vapor from the hands of the individual is referred to as the operator sampling tube 30. The other sampling tube receives air from the environment of the individual. For convenience of reference this sampling tube is referred to as the environment sampling tube 40. Air may be drawn in by any known air-collecting apparatus from the interior of the motor vehicle and directed to the environment sampling tube 40 by means of conduit. For convenience, the conduit is referred to as the environment conduit 52. The air-collector apparatus may be as simple as placement of the open end of the environment conduit 52 in the environment (vehicle interior) to be sampled. Referring now to FIG. 5, therein is illustrated a schematic representation of the conduit network in accordance with a preferred embodiment of the invention. The manifold tube 16, into which the vapor tubes 14 feed, in turn feeds into the collecting conduit 18. The connecting conduit 18 in turn feeds into the operator sampling tube 30. An environment air collector 50 (which, as previously mentioned, is the inlet which collects air from the surrounding environment) is connected to the environment conduit 52. As previously mentioned, the environment conduit 52 is connected to the environment sampling tube 40. The operator sampling tube 30 and environment sampling tube 40 are connected to a mechanism for drawing the vapor and environment air through the network. A suitable mechanism is a vacuum pump 62. Both sampling tubes 30, 40 may be connected to a single vacuum pump 62 by means of a Y-tube 60. Known types of flexible, rigid or semi-rigid or semi-flexible tubing may be used as the connecting conduits 14, 16, 18, 52, 60. A suitable type of tubing is tubing made from an inert type of material that will not noticeably affect the chemical reactions involved. A suitable type of material for the tubing is high-density polyethylene. A suitable vacuum pump and tubing network is one which will enable a finely-variable vacuum to be drawn over a range of 1 to 100 torr. A suitable vacuum pump 62 is model number H-79200-00 manufactured by Cole Parmer. In the preferred embodiment of the invention the network optimally draws the same quantity of gaseous substance (that is, air, vapor and/or air-vapor mixture) through each tube.

Referring now simultaneously to FIGS. 4 and 5, the electrical components of the system will be discussed. The coils 32, 36, 42, 46 may be coiled electrically conductive wire such as nickel chromium. The reference coils 32, 42 are isolated from, and thus are not affected by, the air/vapor passing through the respective tubes 38, 48 by their respective casings 34, 44. The sampling coils 36, 46 are optimally made of the same material as the reference coils 32, 42. The sampling coils 36, 46 are coated with a catalyst which when contacted by a particular substance causes oxidation on the coils. The oxidation in turn causes a negative electrical charge to build up upon the sampling coils 36, 46. In the preferred embodiment discussed herein the chemical substance to be detected is ethanol (which is produced in humans by the consumption and metabolizing of alcohol). In the preferred embodiment, the catalyst of metallic oxide is applied to the coils in a soluble ionic metal medium. When dried and heated to about 250 degrees F. an insoluble metallic oxide film remains on the coil.

A suitable catalyst which interacts with ethanol to cause oxidation is a metal-nonmetal composite such as copper oxide. When the catalyst of copper oxide is contacted by ethanol vapor the ethanol oxidizes causing an excess negative charge to be produced on the sampling coils 36, 46.

Although ethanol is the substance indicative of impairing-substance consumption which has been discussed thus far it is to be noted that other impairing substances, such as cocaine, produce by-products in the human body which are detectable in vapor and which similarly are oxidized by heated metallic-oxide catalysts. For example, the consumption of cocaine produces "amines" which can be interacted with catalysts to promote oxidation.

The presence of oxidized materials on the sampling coils 36, 46 will produce a negative charge buildup on the coils 36, 46 when a potential is applied across the bridge circuitry. When a voltage potential is applied to the coil bridge circuitry (for example by a 6 volt battery as shown) and ethanol vapor is drawn through the system a negative charge resulting from oxidation on the sampling coils will be evidenced by a change in voltage.

Referring now more particularly to FIG. 6, therein is shown in more detail an electronic circuit suitable, for use with a preferred embodiment of a system for monitoring and encumbering use of a hand-operated machine by an impaired individual through detection of toxins in the individual. The bridge circuit is arranged as a constant-current loop more commonly know as a "wheatstone bridge." The bridge has two adjoining sets of coil elements. Each set consists of a reference coil and a sampling coil 32/36, 42/46 symmetrically disposed about a potentiometer P1. A voltage potential is applied across the bridge by a 6 volt battery B3. The battery B3 is made selectively engaged through the switch S3. The potentiometer P1 allows for a variation in the measured initial voltage. This provides the ability to zero or otherwise control the initial voltage output of the bridge while compensating for voltage-balance variations inherent in the bridge circuit. When the bridge circuit is energized by the battery B3 prior to the application of air and vapor to the coils the potentiometer may be used so that the bridge circuit represents a nullity, that is, the voltage difference between the sides of the bridge are net "zero."

The environment coil 46 serves to equalize the circuit and prevent false readings if there happens to be some vapor substance in the environment that might be drawn through the tubing network so as to indicate the presence of a toxin in the operator (through the detection of toxin at the operator coil 36) when there really is not. Another way of viewing the use of the environment coil 46 is that it serves to adjust the reading of the bridge circuit to take into account any generally fluid substances, or more particularly vapor substances, that are present in the environment which might produce a false reading. This consideration is necessary because substances in the environment are also drawn through both the vapor tubes 14 and the environment air collector 50 and environment conduit 52.

Once oxide deposition on the operator coil 36 causes a difference in electrical potential to be present across the bridge this difference in potential, or voltage, $\Delta V$, is applied to a discriminator circuit for processing through resistors R4 and R6. The discriminator circuitry (which is the remainder of the electronic schematic which accompanies the bridge circuit in FIG. 6) converts the charge build-up into a continuous electric current signal which can be measured and calibrated by known electronic components to equate to various ethanol concentrations. The signal output can then be used to initiate a display, a sound generating circuit and/or a circuit which ultimately renders the machine (vehicle) inoperable.

The discriminator circuitry is energized by two 9 volt batteries B1 and B2. Battery B1 is grounded by means of switch S1. Battery B2 is grounded by means of switch S2. Op amp Op1 serves as a differentiator type circuit. The voltage potential from the environment reference leg 40 elements is applied to the inverting input of op amp Op1 while the voltage potential from the operator sampling leg 30 elements is applied at the non-inverting input of op amp Op1.

The output of op amp Op1 is amplified by op amp Op2. The potential from the variable leg component of the potentiometer P1 is applied through the 1 megohm, resistor R4 to the non-inverting input of op amp Op1 and is grounded through the 10 megohm resistor R5. The potential from the environment sampling side of the bridge is applied to the inverting terminal of op amp Op1 through the 1 megohm resistor R6. The inverting terminal of op amp Op2 is grounded through the 1 megohm resistor R2. The non-inverting terminal of op amp Op2 is connected to the 10 megohm resistor R1. Feedback from op amp Op1 passes through resistor R1. Suitable op amps are model numbers 1458 as manufactured and/or sold by Radio Shack. Another suitable amplification component is the AD620 instrumentation amplifier manufactured and/or sold by Analog Devices.

The invention incorporates features to limit as much as possible the inadvertent or intentional circumvention of monitoring. For example, an accurate reading will not be obtained if a machine operator (such as a driver) wears gloves or otherwise uses a device or article which inserts a buffer between the operator's hands and the machine-operating mechanism to be grasped. In a preferred embodiment of the invention the sampling system described above is actuated simultaneously with or in close proximity to actuation of the machine (for example motor vehicle) As a failsafe mechanism the invention employs a pH detector such as that described in U.S. Pat. No. 5,793,292. The disclosure of that patent is hereby incorporated by reference. That application teaches the detection of predetermined pH levels of the secretions from a driver's hands at the steering wheel (or other grasped operating article) as indicative of the presence of hands on the steering wheel or other grasped article. In the preferred embodiment, the pH levels are chosen so as to cover and respond to a range known to be normal for a high percentage of the population. Higher or lower pH ranges relative to the so-called normal range are indicative of an abnormal physiological condition (such as high blood-alcohol concentration) which would interfere with normal driving or other vehicle operational abilities. In the preferred embodiment the pH detector works in conjunction with the vapor-sampling elements such that the system determines through the pH detector whether an individual's hands are in direct contact with the operating article to be grasped. Further, the pH detector provides a means for comparing the output signal of the vapor-sampling circuitry for consistency. For example, an indication of the absence of alcohol by the vapor-sampling circuitry but a reading of the presence of alcohol by the pH detector causes actuation of signals requesting that the operator place his or her uncovered hands upon the article to be grasped. The pH detector may also cause the encumbering circuitry to be energized and actuated such that the same mechanisms are engaged which are engaged when the vapor-detection circuitry detects a predetermined level of toxins.

Another failsafe mechanism incorporated in the present invention is also taught in the aforeside U.S. Pat. No. 5,793,292. That patent teaches a motion detection feature which operates when the vehicle is in motion to detect a predetermined yaw or detectable swerve which is characteristic of improper driving performance, which in turn activates an inertia measuring unit. If the chemical-detecting circuitry previously described does not indicate intoxicating substances but the motion detector receives signals indicative of improper machine operation the motion detector reading causes actuation of signals requesting that the operator place his or her uncovered hands upon the article to be grasped. The motion detector may also cause the encumbering circuitry to be energized and actuated such that the same mechanisms are engaged which are engaged when the vapor-detection circuitry detects a predetermined level of toxins.

As should be apparent from the foregoing specification, the invention is susceptible of being modified with various alterations and modifications which may differ from those which have been described in the preceding specification and description. For example, it is noted that the preferred embodiment of the invention described above utilizes vaporized perspiration, however, it is to be recognized that the invention is also more generally applicable to fluidized perspiration in general which may include perspiration in liquid form as well. Accordingly, the following claims are intended to cover all alterations and modifications which do not depart from the spirit and scope of the invention.

What is claimed is:

1. A system for monitoring and encumbering use of a hand-operated machine by an impaired individual comprising:

means for detecting a pH level of perspiration in the individual's hand when the individual grasps an article for operating the machine;

means for detecting ethanol in perspiration from the individual's hands; and means for providing an electrical signal for energizing a mechanism for encumbering operation of the machine when said means for detecting ethanol detects an amount of ethanol which exceeds a predetermined level or when said means for detecting a pH level detects either no pH level or a pH level indicative of a toxin produced from the consumption of alcohol.

2. The system of claim 1, said means for detecting ethanol in perspiration from the individual's hands comprising:

a detector for receiving fluidized perspiration and producing an electrical signal in proportion to an amount of ethanol present in the fluidized perspiration; and apparatus for drawing through said detector the fluidized perspiration from the hands of an individual when an article for operating the machine is grasped by the individual.

3. The system of claim 1, further comprising a motion detector for detecting a predetermined machine movement which is characteristic of improper machine operation performance and wherein said means for encumbering operation of the machine is engaged when said motion detector detects said machine movement.

4. The system of claim 3, said predetermined machine movement comprising at least one of a predetermined yaw.

5. A system for monitoring and encumbering use of a hand-operated machine by an impaired individual comprising:

a detector for receiving fluidized perspiration and producing an output electrical signal in proportion to an amount of ethanol present in the fluidized perspiration; and apparatus for drawing the fluidized perspiration from the hands of an individual when an article for operating the machine is grasped by the individual through said detector.

6. The system of claim 5, wherein said detector includes an electrical circuit having electrical components which produce an increase in negative electrical charge in proportion to said amount of ethanol.

7. The system of claim 6, wherein said electrical components include coils forming a constant-current loop.

8. The system of claim 7, wherein said constant-current loop comprises a wheatstone bridge.

9. The system of claim 7, wherein said coils are coated with a composite metal-nonmetal catalytic substance.

10. The system of claim 9, said composite metal-nonmetal catalytic substance comprising metallic oxide.

11. The system of claim 5, said detector including discriminator type of electrical circuit having coils which form a part of a constant-current voltage loop which produces an increase in negative electrical charge in proportion to said amount of ethanol and having circuit components which convert said increase in negative electrical charge into said electrical signal.

12. The system of claim 5, said apparatus for drawing the fluidized perspiration from the hands of an individual when an article for operating the machine is grasped by the individual comprises a conduit network including at least one conduit end terminating at a surface of said article and a mechanism for applying a vacuum such that said fluidized perspiration is drawn through said detector.

13. The system of claim 5, further comprising a motion detector for detecting a predetermined machine movement which is characteristic of improper machine operation performance and wherein said means for encumbering operation of the machine is engaged when said motion detector detects said machine movement.

14. The system of claim 13, said predetermined machine movement comprising at least a predetermined yaw.

* * * * *